US012383209B2

(12) United States Patent
Wang (10) Patent No.: US 12,383,209 B2
(45) Date of Patent: Aug. 12, 2025

(54) ROLLOVER DETECTION SYSTEM, METHOD AND STORAGE MEDIUM

(71) Applicant: Luxshare Precision Industry Company Limited, Shenzhen (CN)

(72) Inventor: Guanhsiung Wang, Shenzhen (CN)

(73) Assignee: LUXSHARE PRECISION INDUSTRY CO., LTD., Shenzhen (CN)

( * ) Notice: Subject to any disclaimer, the term of this patent is extended or adjusted under 35 U.S.C. 154(b) by 0 days.

(21) Appl. No.: 18/647,880

(22) Filed: Apr. 26, 2024

(65) Prior Publication Data

US 2024/0366161 A1 Nov. 7, 2024

(30) Foreign Application Priority Data

May 5, 2023 (CN) .......................... 202310497658.7

(51) Int. Cl.
*A61B 5/00* (2006.01)
*A61B 5/01* (2006.01)
(Continued)

(52) U.S. Cl.
CPC .............. *A61B 5/746* (2013.01); *A61B 5/015* (2013.01); *A61B 5/1114* (2013.01);
(Continued)

(58) Field of Classification Search
CPC ....... A61B 5/746; A61B 5/015; A61B 5/1114; A61B 5/7405; A61B 5/747;
(Continued)

(56) References Cited

U.S. PATENT DOCUMENTS

2019/0130720 A1 5/2019 Lui
2020/0163602 A1* 5/2020 Pareddy ............... A61B 5/6807
(Continued)

FOREIGN PATENT DOCUMENTS

CN 104091408 B 4/2015
CN 112315426 A 2/2021
(Continued)

OTHER PUBLICATIONS

Taiwanese Office Action and Search Report for Taiwanese Application No. 112140615, dated Jun. 5, 2024, with English translation.

*Primary Examiner* — Allen C Wong
(74) *Attorney, Agent, or Firm* — Birch, Stewart, Kolasch & Birch, LLP (57) ABSTRACT

A rollover detection system, method and storage medium are provided. The system includes an image acquiring module, an image processing module, a rollover detection subsystem, and an alert module. The image acquiring module is configured to acquire an infrared optical signal of a to-be-monitored object and an analog electrical signal of the infrared optical signal. The image processing module is configured to process the infrared optical signal and the analog electrical signal to obtain a digitalized infrared thermal image. The rollover detection subsystem is configured to perform a rollover detection on a to-be-monitored object according to the infrared thermal image, and determine a rollover detection result. The alert module is configured to generate alert information when the rollover detection result is that a rollover event occurred, push the alert information to an associated application, and synchronize the alert information and a rollover image to the cloud.

10 Claims, 4 Drawing Sheets

(51) Int. Cl.
| | |
|---|---|
| *A61B 5/11* | (2006.01) |
| *G06T 7/11* | (2017.01) |
| *G06T 7/215* | (2017.01) |
| *G06T 7/90* | (2017.01) |
| *G06V 10/60* | (2022.01) |
| *G06V 40/20* | (2022.01) |
| *G08B 21/02* | (2006.01) |
| *H04N 23/11* | (2023.01) |
| *H04N 23/611* | (2023.01) |

(52) U.S. Cl.
CPC ............ *A61B 5/7405* (2013.01); *A61B 5/747* (2013.01); *G06T 7/11* (2017.01); *G06T 7/215* (2017.01); *G06T 7/90* (2017.01); *G06V 10/60* (2022.01); *G06V 40/23* (2022.01); *G08B 21/0208* (2013.01); *H04N 23/11* (2023.01); *H04N 23/611* (2023.01); *A61B 2503/04* (2013.01); *G06T 2207/10024* (2013.01); *G06T 2207/10048* (2013.01); *G06T 2207/30196* (2013.01)

(58) Field of Classification Search
CPC ....... A61B 2503/04; G06T 7/215; G06T 7/11; G06T 7/90; G06T 2207/10024; G06T 2207/10048; G06T 2207/30196; G06V 10/60; G06V 40/23; H04N 23/11; H04N 23/611; G08B 21/0208
USPC .......................................................... 348/77
See application file for complete search history.

(56) References Cited

U.S. PATENT DOCUMENTS

2022/0178981 A1\* 6/2022 Messano ............ G01R 29/0857
2023/0222887 A1\* 7/2023 Muhsin ................ G08B 21/043

FOREIGN PATENT DOCUMENTS

| CN | 112542235 A | 3/2021 |
| TW | 201137795 A1 | 11/2011 |
| TW | M480134 U | 6/2014 |

\* cited by examiner

ROLLOVER DETECTION SYSTEM, METHOD AND STORAGE MEDIUM

CROSS-REFERENCE TO RELATED APPLICATION(S)

This application claims priority to Chinese Patent Application No. 202310497658.7 filed on May 5, 2023, the disclosure of which is incorporated herein by reference in its entirety.

TECHNICAL FIELD

The present invention relates to the field of home safety and protection technologies, and more particularly, to a rollover detection system, a rollover detection method and a storage medium.

BACKGROUND

In the early stage of infant development, if an infant lies on the ground and rolls over or lies in a prone position after drinking milk, the infant is apt to emit milk, and emesis of the infant may cause obstruction of the respiratory tract and may further cause asphyxiation of the infant. It can be seen that the infant needs to be taken care of by a caregiver at all times, but the infant cannot have the caregiver to keep him company at all times. Therefore, in home safety and protection, there is a need for a method and system for monitoring rollover of the infant.

Currently, in the conventional method or system for detecting whether an infant rolled over or not, it is generally based on a coordinate of a head position, an oral position and a nose position of the infant to determine whether the infant rolled over. However, the coordinates of positions of the mouth and the nose are very close to each other, which is apt to cause a false determination on whether the infant rolled over or not and results in a caregiver's failing to spot a dangerous situation of the infant in time. Therefore, the conventional method or system has a low insurance on the safety of the infant.

SUMMARY

A rollover detection system, a rollover detection method and a storage medium are provided according to the present invention, which realizes non-contact rollover detection on a to-be-monitored object, reduces errors of rollover detection, improves the accuracy of rollover detection, and ensures the safety of the to-be-monitored object.

According to a first aspect, a rollover detection system is provided according to an embodiment of the present disclosure, which includes an image acquiring module, an image processing module, a rollover detection subsystem and an alert module.

The image acquiring module is configured to acquire an infrared optical signal of a to-be-monitored object and an analog electrical signal of the infrared optical signal and transmit the infrared optical signal and the analog electrical signal of the infrared optical signal to the image processing module.

The image processing module is configured to process the infrared optical signal and the analog electrical signal of the infrared optical signal to obtain a digitalized infrared thermal image, and transmit the digitalized infrared thermal image to the rollover detection subsystem.

The rollover detection subsystem is configured to perform a rollover detection on the to-be-monitored object according to the digitalized infrared thermal image, and determine a rollover detection result of the to-be-monitored object.

The alert module is configured to generate rollover alert information in response to the rollover detection result being a rollover event, push the rollover alert information to an associated application, and synchronize the rollover alert information and the rollover image to a cloud.

In a second aspect, a rollover detection method is provided according to an embodiment of the present disclosure, which includes as follows.

An infrared optical signal of a to-be-monitored object and an analog electrical signal of the infrared optical signal are acquired.

The infrared optical signal and the analog electrical signal of the infrared optical signal are processed to obtain a digitalized infrared thermal image.

A rollover detection is performed on the to-be-monitored object according to the digitalized infrared thermal image, and a rollover detection result of the to-be-monitored object is determined.

Rollover alert information is generated in response to the rollover detection result being a rollover event, the rollover alert information is pushed to an associated application, and the rollover alert information and the rollover image are synchronized to a cloud.

In a third aspect, a computer readable storage medium is provided according to an embodiment of the present disclosure. The computer-readable storage medium stores a computer instruction, where the computer instruction is used to cause a rollover detection system to implement the rollover detection method according to the embodiment in the second aspect when the rollover detection system performs the computer instruction.

A rollover detection system, a rollover detection method and a storage medium provided in the embodiments of the present invention include an image acquiring module, an image processing module, a rollover detection subsystem, and an alert module. The image acquiring module is configured to acquire an infrared optical signal of a to-be-monitored object and an analog electrical signal of the infrared optical signal and transmit the infrared optical signal and the analog electrical signal of the infrared optical signal to the image processing module; the image processing module is configured to process the infrared optical signal and the analog electrical signal of the infrared optical signal to obtain a digitalized infrared thermal image, and transmit the digitalized infrared thermal image to the rollover detection subsystem; the rollover detection subsystem is configured to perform a rollover detection on a to-be-monitored object according to the digitalized infrared thermal image, and determine a rollover detection result of the to-be-monitored object; and the alert module is configured to generate rollover alert information when the rollover detection result is that a rollover event occurred, push the rollover alert information to an associated application, and synchronize the rollover alert information and the rollover image to a cloud. The above technical solution realizes a non-contact rollover detection on a to-be-monitored object, reduces errors of rollover detection, improves the accuracy of rollover detection, and ensures the safety of the to-be-monitored object.

It is to be understood that the contents described in this part are not intended to identify key or important features of the embodiments of the present disclosure, rather than limiting the scope of the present disclosure. Other features of the present disclosure will become readily understood through the description hereinafter.

BRIEF DESCRIPTION OF DRAWINGS

To illustrate technical solutions in embodiments of the present invention more clearly, drawings used in description of the embodiments are briefly described hereinafter. Apparently, the drawings described below merely illustrate some embodiments of the present invention, and the person of ordinary skill in the art can obtain other drawings based on these drawings on the premise that no creative efforts are made.

DETAILED DESCRIPTION

For enabling the person skilled in the art to better understand the solutions of the present invention, the technical solutions in embodiments of the present invention are described clearly and completely in conjunction with the drawings in embodiments of the present invention. Apparently, the embodiments described below are part, rather than all, of the embodiments of the present invention. Based on the embodiments in the present invention, all other embodiments obtained by the person skilled in the art on the premise that no creative efforts are made are within the scope of the present invention.

It is to be noted that the terms "first", "second", "target" and the like in the description, claims and the above drawings of the present invention are intended to distinguish between similar objects and are not necessarily used to describe a particular order or sequence. It is to be appreciated that the data used in this way is interchangeable where appropriate so that the embodiments of the present invention described herein may also be implemented in a sequence besides those sequences illustrated or described herein. Furthermore, terms such as "include", "have"; and any deformation thereof, are intended to cover non-exclusive inclusion, e.g., a process, method, system, product, or device including a series of steps or units is not necessarily limited to those steps or units expressly listed, but may include other steps or units not expressly listed or inherent to such process, method, system, product or device.

First Embodiment

Figure 1:
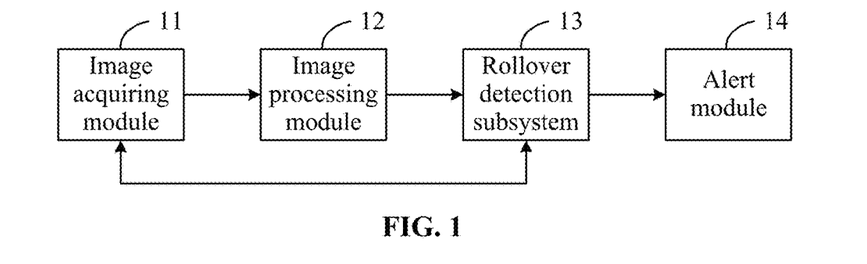
FIG. 1 is a block diagram showing the structure of a rollover detection system according to a first embodiment of the present invention.

FIG. 1 is a block diagram showing the structure of a rollover detection system according to the first embodiment of the present invention. This embodiment is applicable to a case in which whether a to-be-monitored object rolled over is detected. The rollover detection system is implemented in the form of a combination of hardware and software.

As shown in FIG. 1, the rollover detection system includes an image acquiring module 11, an image processing module 12, a rollover detection subsystem 13 and an alert module 14.

The image acquiring module 11 is configured to acquire an infrared optical signal of a to-be-monitored object and an analog electrical signal of the infrared optical signal and transmit the infrared optical signal and the analog electrical signal of the infrared optical signal to the image processing module 12.

The image processing module 12 is configured to process the infrared optical signal and the analog electrical signal of the infrared optical signal to obtain a digitalized infrared thermal image, and transmit the digitalized infrared thermal image to the rollover detection subsystem 13.

The rollover detection subsystem 13 is configured to perform a rollover detection on the to-be-monitored object according to the digitalized infrared thermal image, and determine a rollover detection result of the to-be-monitored object.

The alert module 14 is configured to generate rollover alert information in response to the rollover detection result being a rollover event, push the rollover alert information to an associated application, and synchronize the rollover alert information and the rollover image to a cloud.

In this embodiment, the image acquiring module 11 is connected to the image processing module 12 to transmit an acquired optical signal and an electrical signal to the image processing module 12. The image processing module 12 is connected to the rollover detection subsystem 13 to transmit a digitalized infrared thermal image generated after the processing to the rollover detection subsystem 13 for rollover detection. The rollover detection subsystem is connected to the alert module 14 to transmit a detection result of the rollover detection performed on the to-be-monitored object to the alert module 14. The alert module 14 is connected to the rollover detection subsystem 13 to receive the rollover detection result transmitted by the rollover detection subsystem 14, and generate rollover alert information when the rollover detection result detected by the rollover detection subsystem is that a rollover event occurred, and push the rollover alert information to an associated application, and synchronize the alert information and the rollover image to a cloud.

The image acquiring module 11 is configured to, when a rollover detection requirement for a to-be-monitored object is generated, automatically acquire the infrared optical signal in a region where the to-be-monitored object is located, convert the optical signal into analog electrical signal (analogous electrical signal), and transmit the infrared optical signal and the converted analog electrical signal to the image processing module 12 for further image processing.

The rollover detection requirement for the to-be-monitored object may be periodic cyclic acquisition requirements determined according to a preset period, or may be an acquisition requirement manually triggered by a related person through an associated application. A specific rollover detection requirement is determined according to practical conditions, which is not limited in this embodiment. It may be appreciated that the image acquiring module 11 can always obtain clear infrared optical signal and converted analog electrical signal regardless of whether the ambient light is bright or dark.

The image processing module 12 is configured to receive the infrared optical signal and the analog electrical signal of the infrared optical signal transmitted by the image acquiring module 11. After the infrared optical signal and the analog electrical signal are received, and in order to enable the rollover detection subsystem 13 to more accurately implement the rollover detection on the to-be-monitored object, basic signal and image processing is performed on the analog electrical signal of the infrared optical signal in advance to obtain a digitalized infrared thermal image with clearer features. Specifically, the analog electrical signal is converted into a digital electrical signal, and corresponding basic image processing, such as filtering, denoising, enhancement or restoration, is performed on the converted digital electrical signal to generate a digitalized infrared thermal image. The digitalized infrared thermal image generated after the processing is transmitted to the rollover detection subsystem 13.

The rollover detection subsystem 13 is configured to receive and store the digitalized infrared thermal image transmitted by the image processing module 12 and having subjected to the basic signal and image processing, and perform processing such as segmentation and feature extraction on the acquired infrared thermal image to determine a body region of the to-be-monitored object, and further determine a head region, a hand region, an origin position coordinate, a head position coordinate, and a hand position coordinate in the body region of the to-be-monitored object, and determine a rollover detection result of the to-be-monitored object according to the position change of the head region between two adjacent periods and the position change of the hand region of the to-be-monitored object between two adjacent periods, and transmit the rollover detection result to the alert module 14 after the rollover detection result of the to-be-monitored object is determined.

The alert module 14 is configured to receive the rollover detection result transmitted by the rollover detection subsystem 13, and perform a corresponding execution operation according to the rollover detection result. When the rollover detection result is that a rollover event did not occur, the alert module 14 does not operate; and when the rollover detection result is that a rollover event occurred, the alert module 14 generates rollover alert information and push the rollover alert information to an associated application and synchronize the rollover alert information and the rollover image to a cloud so as to timely alert a caregiver and a related care mechanism of the to-be-monitored object, so that the caregiver and the related care mechanism can respond to the rollover event of the to-be-monitored object after receiving the rollover alert information, and take corresponding care of the to-be-monitored object in time.

A rollover detection system according to this embodiment includes an image acquiring module, an image processing module, a rollover detection subsystem and an alert module. The image acquiring module is configured to acquire an infrared optical signal of a to-be-monitored object and an analog electrical signal of the infrared optical signal and transmit the infrared optical signal and the analog electrical signal of the infrared optical signal to the image processing module. The image processing module is configured to process the infrared optical signal and the analog electrical signal of the infrared optical signal to obtain a digitalized infrared thermal image, and transmit the digitalized infrared thermal image to the rollover detection subsystem. The rollover detection subsystem is configured to perform a rollover detection on the to-be-monitored object according to the digitalized infrared thermal image, and determine a rollover detection result of the to-be-monitored object. The alert module is configured to generate rollover alert information when the rollover detection result is that a rollover event occurred, push the rollover alert information to an associated application, and synchronize the rollover alert information and the rollover image to a cloud. According to the above technical solution, the image acquiring module can acquire the infrared optical signal of a region, where the to-be-monitored object is located, adaptively in various environments, the image processing module performs corresponding image processing in advance before the rollover detection is performed on the to-be-monitored object, to allow the infrared thermal image input to the rollover detection subsystem to be clearer in features, the rollover detection subsystem monitors positions of the head region and the hand region of the to-be-monitored object, and determines the rollover detection result according to the position offset situations of the head region and the hand region of the to-be-monitored object, thereby effectively enhancing the accuracy of the rollover detection, reducing the errors of the rollover detection, and when the rollover detection result is that a rollover event occurred, the alert module can timely generate alert information to notify the caregiver of the to-be-monitored object, thereby effectively improving the personal safety of the to-be-monitored object. With the above technical solution, a non-contact rollover detection on a to-be-monitored object is realized, the errors of the rollover detection are reduced, the accuracy of the rollover detection is improved, and the safety of the to-be-monitored object is guaranteed.

Figure 2:
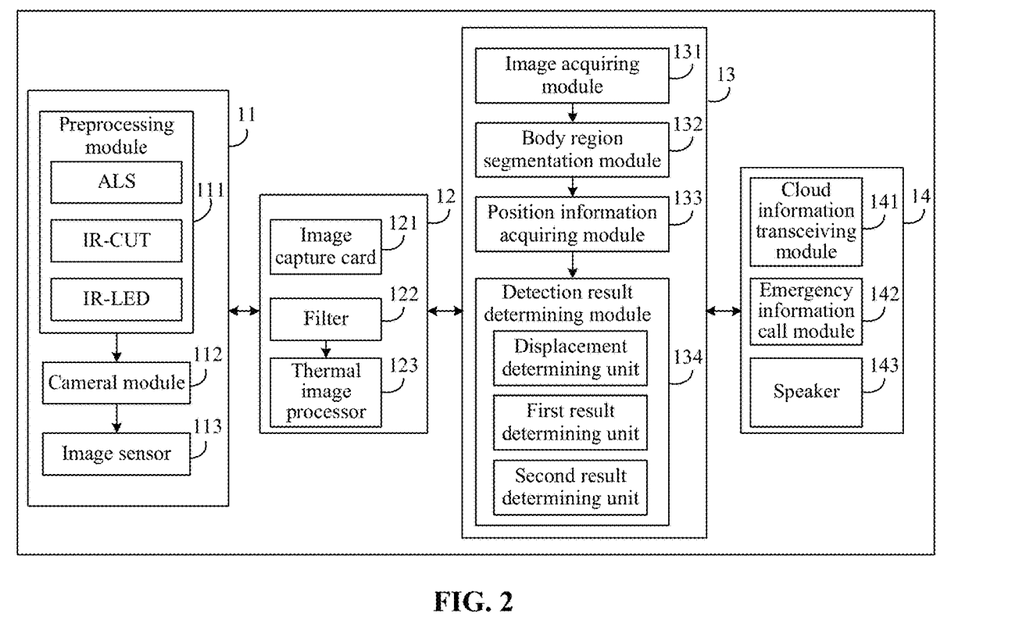
FIG. 2 is a block diagram showing the structure of another rollover detection system according to the first embodiment of the present invention.

As a first alternative embodiment of the embodiment, on the basis of the above embodiment, as shown in FIG. 2, the image acquiring module 11 includes a preprocessing module 111, a camera module 112 and an image sensor 113.

The preprocessing module 111 is configured to assist the camera module 112 in acquiring optical signals in a dark condition.

The camera module 112 is configured to acquire an optical signal.

The image sensor 113 is configured to converge the optical signal for forming an infrared thermal image, and convert the optical signal into an analog electrical signal.

In this embodiment, the preprocessing module 111 is connected to the camera module 112, and assists the camera module 112 in acquiring the optical signal when the illuminance is insufficient. The camera module 112 is connected to the image sensor 113, and transmits the acquired optical signal to the image sensor 113. The image sensor 113 is connected to the camera module 112, receives the optical signal transmitted by the camera module 112, and performs conversion of the optical signal into the electrical signal.

The preprocessing module 111 is configured to assist the camera module 112 in acquiring the optical signal under the condition of insufficient illuminance. It may be appreciated that the preprocessing module 111 may also be directly connected to the rollover detection subsystem 13. The preprocessing module 111 senses the current ambient light condition, and transmits the currently sensed ambient light condition to the rollover detection subsystem 13. The rollover detection subsystem 13 controls the preprocessing module 111 to operate to adjust the camera module 112 so that the camera module 112 can operate normally and acquire optical signals even under the condition of insufficient illumination.

The camera module 112 is configured to acquire optical signals in a region where the to-be-monitored object is located, and to cause the acquired optical signals to converge to the image sensor 113.

The image sensor 113 is configured to receive and converge the optical signal acquired by the camera module 112, and convert the optical signal into the analog electrical signal (analogous electrical signals). In a conventional camera, a film is a photosensitive material, and the film will record a captured image after subjected to a certain chemical treatment. In the digital camera, the image sensor 113 replaces the function of the film to form an electronic image. The image sensor 113 may be a charge coupled device (CCD) or a complementary metal-oxide semiconductor (CMOS), which is not limited in the embodiment.

Specifically, the image sensor 113 receives the optical signal transmitted by the camera module 112, and converges the optical signal on the CMOS/CCD, and converts the infrared optical signal into the analog electrical signal. The image sensor 113, after completing the conversion of the infrared optical signal into the analog electrical signal, transmits the infrared optical signal and the analog electrical signal of the infrared optical signal to the image processing module 12.

Further, as shown in FIG. 2, the preprocessing module 111 includes an ambient light sensor, an infrared cut-off filter, and an infrared diode unit.

The ambient light sensor (ALS) is configured to detect illuminance of an environment. When ambient light of a region in which the to-be-monitored object is located becomes dark, the ALS can detect the illuminance of the current environment and transmit, according to the increase or decrease of the illuminance of the environment, a corresponding current signal to notify the rollover detection subsystem 13.

The infrared cut-off filter (IR-CUT) is configured to automatically switch a filter to achieve image denoising when illuminance is insufficient, thereby achieving an optimum effect of the image.

The infrared diode unit (IR-LED) is configured to emit infrared light and receive infrared information of infrared bands emitted from an environment and an object illuminated by the infrared light. Specifically, the IR-LED includes an infrared transmitter diode (IR Transmitter LED) for emitting infrared light and an infrared receiving diode (IR Receiver LED) for identifying infrared information and transmitting the identified infrared information to the camera module 112.

Specifically, since the image sensor 113 (CCD/CMOS) can recognize most wavelengths of lights, the color output by the image sensor 113 is different from the color seen by the naked eye due to the action of various wavelengths of lights. In the case of darkness or insufficient illuminance, the image sensor 113 cannot make full use of the lights, so that background snow noise exists in the sensed image information. Therefore, the ALS is required to sense the illuminance change, convert the illuminance change into current information and transmit the current information to the rollover detection subsystem 13 to determine places in darkness or with insufficient illuminance in the current environment, and the rollover detection subsystem 13 transmits an instruction through an I2C interface to control the IR-CUT to automatically switch the filter to reduce the noise of the image caused by insufficient illuminance, so as to enable the image to have an optimal effect.

When the ALS determines that the illuminance is low or it is in the dark, the rollover detection subsystem 13 may activate the IR Transmitter LED and the IR Receiver LED in the IR-LED. The human body may emit heat, the heat is approximate to the color temperature close to red in the microwave bands, therefore, after the IR Transmitter LED emits the infrared light, the environment and the object in the region where the to-be-monitored object is located in the dark may also correspondingly emit the infrared bands, and the IR Receiver LED receives the infrared information of these infrared bands and transmits the infrared information to the camera module 112.

As a second alternative embodiment of the embodiment, on the basis of the above embodiment, as shown in FIG. 2, the image processing module 12 includes an image capture card 121, a filter 122, and a thermal image processor 123.

The image capture card 121 is configured to convert the analog electrical signal into digital electrical signal and perform image digitalization processing, and transmit the converted digital electrical signal to the rollover detection subsystem 13 to store the converted digital electrical signal.

The filter 122 is configured to filter the analog electrical signal and transmit the filtered analog electrical signal to the thermal image processor 123.

The thermal image processor 123 is configured to convert the analog electrical signal of the infrared thermal image into the digital electrical signal and transmit the digital electrical signal to the rollover detection subsystem 13.

In this embodiment, the image capture card 121 is connected to the rollover detection subsystem 13, receives the infrared optical signal and the analog electrical signal of the infrared optical signal from the image acquiring module 11, and transmits the digital electrical signal (digitalized electrical signal) of the infrared optical signal after being processed to the rollover detection subsystem 13 to store the converted digital electrical signal. The filter 122 is connected to the thermal image processor 123 and acquires the analog electrical signal from the image acquiring module 11, and then transmits filtered analog electrical signal to the thermal image processor 123. The thermal image processor 123 is connected to the rollover detection subsystem 13, acquires the analog electrical signal transmitted by the filter 122, and then converts the analog electrical signal into digital electrical signal, and transmits the digital electrical signal to the rollover detection subsystem 13.

The image capture card 121 is configured to acquire the analog electrical signal transmitted by the image acquiring module 11, perform analog/digital conversion processing on the analog electrical signal to obtain digital electrical signal, perform basic image digitalization processing on the digital electrical signal to generate a digitalized infrared thermal image, and transmits the digitalized digital information to the rollover detection subsystem 13 to store the digitalized digital information, so that the rollover detection subsystem 13 can invoke corresponding information in time when a rollover detection requirement is generated, and read the image for comparison.

The filter 122 is configured to acquire the analog electrical signal transmitted by the image acquiring module 11, perform filtering processing on the analog electrical signal, filter out unnecessary background noise, and transmit the filtered analog electrical signal to the thermal image processor 123.

The thermal image processor 123 is configured to receive filtered analog electrical signal transmitted by the filter, perform post-processing such as analog/digital conversion and color adjustment on the analog electrical signal, and then transmit a digitalized infrared thermal image generated after the processing to the rollover detection subsystem 13.

As a third alternative embodiment of the embodiment, on the basis of the above embodiments, as shown in FIG. 2, the rollover detection subsystem 13 includes an image acquiring module 131, a body region segmentation module 132, a position information acquiring module 133 and a detection result determining module 134.

The image acquiring module 131 is configured to acquire a digitalized infrared thermal image of a to-be-monitored object according to a preset period.

The body region segmentation module 132 is configured to segment a body region of the to-be-monitored object in the digitalized infrared thermal image according to color temperatures of the digitalized infrared thermal image.

The position information acquiring module 133 is configured to determine a head region and a hand region of the to-be-monitored object from the body region of the to-be-monitored object in the digitalized infrared thermal image, and relevant position information of the to-be-monitored object; and the related position information includes an origin position coordinate, a head position coordinate, and a hand position coordinate.

The detection result determining module 134 is configured to determine the rollover detection result of the to-be-monitored object according to a change of the related position information between two adjacent periods.

In this embodiment, the image acquiring module 131 is connected to the body region segmentation module 132, and after acquiring the digitalized infrared thermal image transmitted by the image processing module 12, the image acquiring module 131 transmits the digitalized infrared thermal image to the body region segmentation module 132. The body region segmentation module 132 is connected to the position information acquiring module 133, and is configured to position the position coordinate of the body region of the to-be-monitored object according to the body region of the to-be-monitored object after the body region of the to-be-monitored object is segmented, so as to obtain relevant position information. The detection result determining module 134 is connected to the position information acquiring module 133 and is configured to perform rollover detection on the to-be-monitored object according to the relevant position information of the to-be-monitored object.

The image acquiring module 131 is configured to acquire, from the image processing module 12, a digital electrical signal (digitalized infrared thermal image) of infrared optical signal of a region where the to-be-monitored object is located according to a preset periodic time, where the preset periodic time may be one hour or one minute, and the specific time is determined according to practical requirements, which is not limited in this embodiment. It will be appreciated that the preset period may be the same as the frequency at which the image acquiring module 11 acquires the analog electrical signal (analogous infrared thermal image) of the infrared optical signals, that is, the period frequency at which the image acquiring module 131 in the rollover detection subsystem 13 acquires the infrared thermal image information corresponds to the period frequency at which the image acquiring module 11 acquire the infrared thermal image information.

The image acquiring module 131 may also be understood as a module having a storage function, for example, a memory, which acquires a digital infrared thermal image transmitted by the image processing module 12 and stores the digital infrared thermal image, so that other modules in the rollover detection subsystem 13 can invoke the digitalized infrared thermal image when performing rollover detection.

The body region segmentation module 132 is configured to segment the digitalized infrared thermal image according to the color temperatures of the digitalized infrared thermal image acquired by the image acquiring module 131 to determine the body region of the to-be-monitored object. The segmentation method for the infrared thermal image may be a region growth algorithm or other methods, which is not limited in this embodiment.

Figure 3:
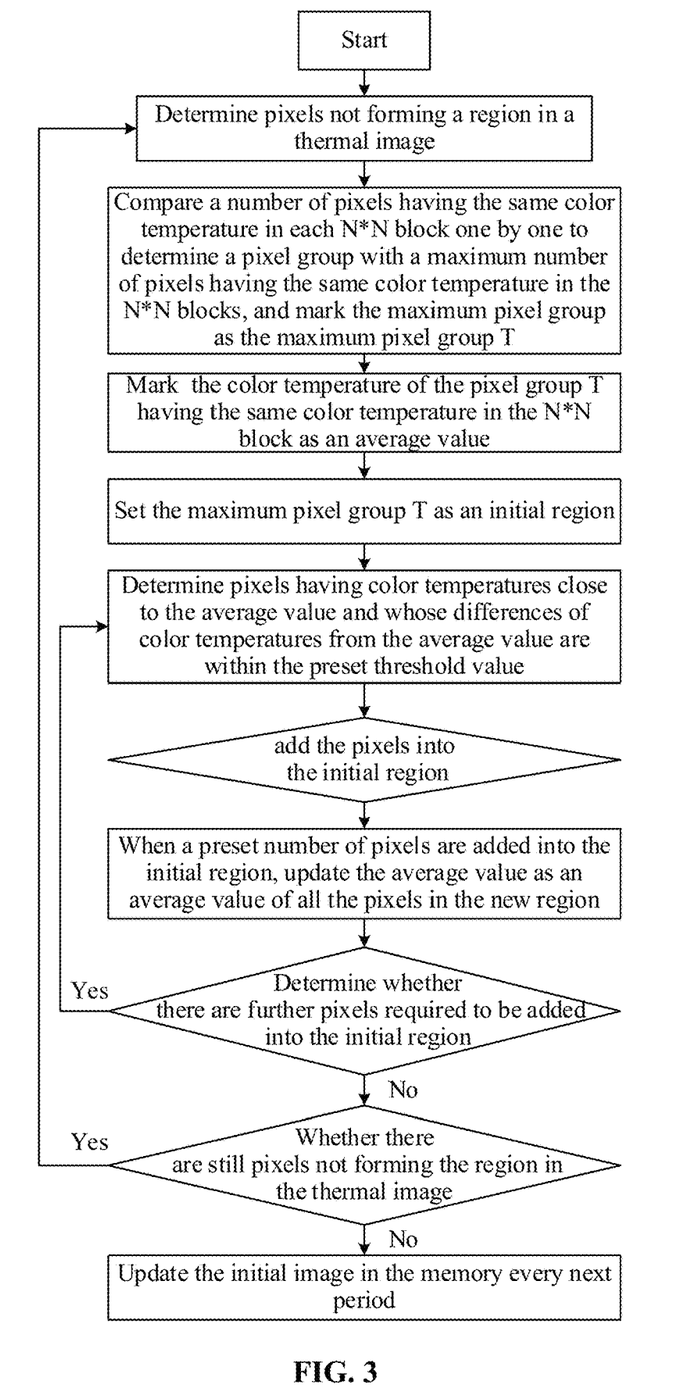
FIG. 3 is a flow chart showing the operation of a body region segmentation module involved in a rollover detection system according to the first embodiment of the present invention.

Specifically, FIG. 3 is a flow chart showing the operation of the body region segmentation module involved in a rollover detection system according to the first embodiment of the present invention. As shown in FIG. 3, the body region segmentation module 132 performs an operation on the received digitalized infrared thermal image, subjected to the filtering and denoising processing, according to a preset segmentation method (for example, a region growth algorithm), and separates and segments the human-type region from the surrounding environment in the infrared thermal image. First, pixels not forming the region are determined, pixels having the same color temperature can be classified into the same region. A N×N block is used as a unit for comparison, a maximum pixel group having the same color temperature in the N×N block is determined and indicated by T, the color temperature of the pixel group T having the same color temperature is indicated by an average value Avg, and that the pixel group T is set as an initial region. A pixel group around the initial region is determined, and pixels with color temperatures close to the average value Avg and whose differences of color temperatures from the average value Avg are within the preset threshold value of the maximum pixel group T are added to the region T. If every preset value (for example, 50) of pixels with the same color temperature are freshly added to the region T to form a new region T', the average value Avg is updated to a new average value Avg' of all the pixels in the T'. Whether there are still pixels to be added into the initial region is determined, and if there is no other pixel having close color temperature to be added into the T', the human-shaped region having close color temperature may be segment from the surrounding environment having a relatively large color temperature difference. The initial image in the memory is updated every other period (e.g., F minutes).

The position information acquiring module 133 is configured to determine the head region and the hand region, and the origin position coordinate, the head position coordinate, and the hand position coordinate of the to-be-monitored object from the body region of the to-be-monitored object according to the color temperatures after the body region of the to-be-monitored object is determined. The origin position coordinate can be understood as the coordinate of the center position of the entire body-shaped region of the to-be-monitored object. The head position coordinate may be understood as the coordinate of the center position of the head region of the to-be-monitored object. The hand position coordinate may be understood as the coordinate of the center position of the hand region of the to-be-monitored object. The center position may be a center, a center of gravity, the orthocenter, or the like of a region, which is not limited in the embodiment.

It may be appreciated that the method for determining the head region and the hand region and their relevant position information from the body region of the to-be-monitored object may be a block comparison algorithm or other methods, which is not limited in this embodiment.

The detection result determining module 134 is configured to determine the rollover detection result of the to-be-monitored object according to whether the change of the origin position coordinate, the head position coordinate and the hand position coordinate of the infrared thermal images of the to-be-monitored object between two adjacent periods is within a preset change range. If the change of the relevant position information of the infrared thermal images of the to-be-monitored object between the two adjacent periods is within the preset change range, it can be determined that the rollover detection result is that a rollover event did not occur; and if the position change of any relevant position information of the infrared thermal images of the to-be-monitored object in the two adjacent periods exceeds the preset change range, it can be determined that the rollover detection result is that a rollover event occurred. The rollover detection result of the to-be-monitored object, after being determined, is transmitted to the alert module 14.

Optionally, the position information acquiring module 133 is specifically configured to do as follows.

a1) The position information acquiring module 133 is specifically configured to determine, according to a body region of the to-be-monitored object, a rectangular region corresponding to the body region.

Figure 4:
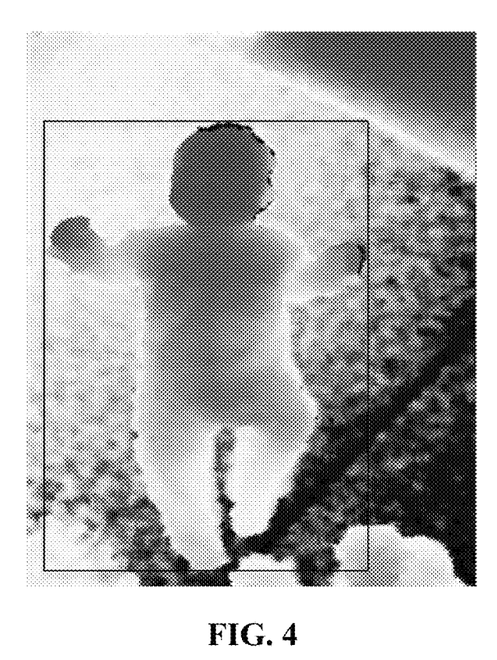
FIG. 4 is a display view showing illustratively a rectangular region corresponding to a body region of a to-be-monitored object involved in a rollover detection system according to the first embodiment of the present invention.

Specifically, FIG. 4 is a display view showing illustratively a rectangular region corresponding to a body region of a to-be-monitored object involved in the rollover detection system according to the first embodiment of the present invention. As shown in FIG. 4, a rectangular region of a width (U) and a length (E) corresponding to the human-shaped body region is determined based on the human-shaped region segmented by the body region segmentation module 132.

b1) The position information acquiring module 133 is specifically configured to determine a center point position of the to-be-monitored object according to a side length of the rectangular region, and determine the center point position as an origin position, and acquire the origin position coordinate.

Specifically, according to the side lengths U and E of the rectangular region, the intersection position of the line connecting the center points of the long sides of the rectangular region and the line connecting the center points of the short sides of the rectangular region is determined as the center point position of the rectangular region, and is determined as the origin position of the to-be-monitored object, and the origin position coordinate of the origin position is set as (0, 0). After the coordinate of the origin position is determined, coordinate axes are constructed in the horizontal direction and the vertical direction, and four quadrants of the rectangular region are established.

c1) The position information acquiring module 133 is specifically configured to determine a head region and a hand region of the to-be-monitored object according to color temperatures in the rectangular region.

The to-be-monitored object may emit heat by itself, and heat emitted from the infant may be seen whatever in daytime or at night from the view of infrared light, and heat may form a heat region, the heat region has a difference between high and low temperatures, thus forming the thermal image. In the thermal image seen from the view of infrared light, portions in the thermal image where the color temperature tends to be more red represents a higher temperature, for example, the head, the hand or the feet of the to-be-monitored object, and portions in the thermal image where the color temperature tends to be more blue represents a lower temperature, for example, background articles.

Specifically, red color temperature regions are determined based on the color temperatures in the rectangular region, and the region corresponding to the head and the regions corresponding to the two hands, that is, the head region and the hand regions, are determined based on region sizes of the red color temperature regions.

d1) The position information acquiring module 133 is specifically configured to determine the head position coordinate and the hand position coordinate according to the origin position coordinate.

Figure 5:
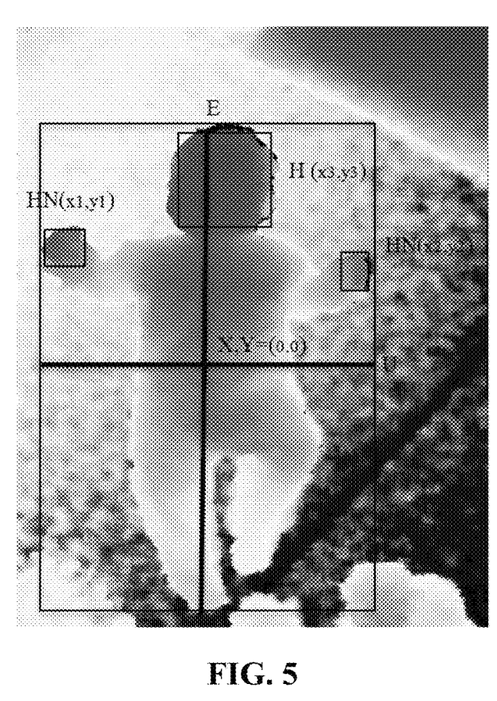
FIG. 5 is a display view showing illustratively a rectangular region, a head region, a hand region, a head position coordinate, hand position coordinates and an origin position coordinate involved in a rollover detection system according to the first embodiment of the present invention.

Specifically, FIG. 5 is a display view showing illustratively a rectangular region, a head region, hand regions, head position coordinate, hand position coordinates and origin position coordinate involved in a rollover detection system according to the first embodiment of the present invention. As shown in FIG. 5, coordinate corresponding to a center position of the head region and coordinates corresponding to center positions of the hand regions determined according to the origin position coordinate (0, 0), are respectively determined as the head position coordinate and the hand position coordinates, where the hand position coordinates are HN (x1, y1) and HN (x2, y2), respectively; and the head position coordinate is H (x3, y3).

Optionally, as shown in FIG. 2, the detection result determining module 134 includes a displacement determining unit, a first result determining unit and a second result determining unit.

The displacement determining unit is configured to determine whether a displacement of the origin position coordinate between the two adjacent periods and a displacement of the head position coordinate between the two adjacent periods are within a first preset range.

The first result determining unit is configured to determine a rollover detection result of the to-be-monitored object to be that a rollover event occurred when the displacement of the origin position coordinate between the two adjacent periods and the displacement of the head position coordinate between the two adjacent periods are within the first preset range and the hand position coordinate of the two adjacent periods are symmetric with respect to the center.

The second result determining unit is configured to determine a rollover detection result of the to-be-monitored object when at least one of the displacement of the origin position coordinate between two adjacent periods and the displacement of the head position coordinate between two adjacent periods does not meet the first preset range.

In this embodiment, whether the displacement of the origin position coordinate between the two adjacent periods and the displacement of the head position coordinate between the two adjacent periods are within the first preset range is determined by the displacement determining unit; if the displacement of the origin position coordinate between the two adjacent periods and the displacement of the head position coordinate between the two adjacent periods are within the first preset range, the first result determining unit is configured to determine a rollover detection result; and if any one of the displacement of the origin position coordinate between the two adjacent periods and the displacement of the head position coordinate between the two adjacent periods is not within the first preset range, the second result determining unit is configured to determine a rollover detection result.

The displacement determining unit is configured to determine whether the displacement of the origin position coordinate in the digitalized infrared thermal images obtained between the two adjacent periods and the displacement of the head position coordinate in the digitalized infrared thermal images obtained between the two adjacent periods are within a first preset range, where the first preset range can be understood as a preset offset range for the origin position coordinate and the head position coordinate, for example, the first preset range may be a distance range within half the width (U/2) of the rectangular region.

Illustratively, the first preset range is (U/4~U/2), and it is determined whether or not the origin position coordinate (X, Y)=(0,0) of the rectangular region is shifted to approximately half of the body width to change the origin position coordinate as (X, Y)=(U/4~U/2, 0) or (−U/2~−U/4, 0). If it is determined that the origin position coordinate (X, Y)=(0, 0) of the rectangular region are shifted to approximately half the body width, it may be determined that the to-be-monitored object is rolled left or rolled right; at the same time, it is necessary to also determine whether the head position coordinate is shifted to approximately half of the body width, which is changed from H (x3, y3) to H (x3+U/4~x3+U/2, y3) or H (x3−U/2~x3−U/4, y3). Determining whether the original position coordinate and the head position coordinate are shift or not, can effectively avoid misjudgment of the phenomenon of rotation (but not rolling over the body) such as body moving without head moving, and effectively improve accuracy of the rollover detection.

The first result determining unit is configured to determine the rollover detection result of the to-be-monitored object to be that a rollover event occurred when the displacement of the origin position coordinate between two adjacent periods and the displacement of the head position coordinate between two adjacent periods are within the first preset range and the hand position coordinate of the two adjacent periods are symmetric with respect to the center.

Illustratively, if the origin position coordinate is changed from (X, Y)=(0,0) to (U/4~U/2, 0) or (−U/2~−U/4, 0), and the head position coordinate is changed from H (x3, y3) to H (x3+U/4~x3+U/2, y3) or H (x3−U/2~x3−U/4, y3), then it is determined whether the hand position coordinate is shifted or not, and it is determined whether the hand position coordinate is changed from HN (x1, y1) to HN (−x1,−y1) or from HN (x2, y2) to HN (−x2,−y2). If the origin position coordinate is changed from (x, y)=(0,0) to (U/4~U/2, 0) or (−U/2~−U/4, 0), the head position coordinate is changed from H (x3, y3) to H (x3+U/4~x3+U/2, y3) or H (x3−U/2~x3−U/4, y3), and the hand position coordinate is changed from HN (x1, y1) to HN (−x1,−y1) or from HN (x2, y2) to HN (−x2,−y2), it is determined that the rollover detection result of the to-be-monitored object is that a rollover event occurred.

The second result determining unit is configured to determine a rollover detection result of the to-be-monitored object when at least one of the displacement of the origin position coordinate between two adjacent periods and the displacement of the head position coordinate between two adjacent periods does not meet the first preset range. Specifically, when the displacement of the origin position coordinate and the displacement of the head position coordinate do not both meet the first preset range in the infrared thermal images between two adjacent periods, it is possible to determine that the to-be-monitored object has a turning around event or a displacement event, whereby the rollover detection result of the to-be-monitored object is further determined by means of the origin position coordinate and the hand position coordinate.

Further, the second result determining unit is specifically configured to do as follows a2) The second result determining unit is specifically configured to determine, when at least one of the displacement of the origin position coordinate between two adjacent periods and the displacement of the head position coordinate between two adjacent periods does not meet the first preset range, whether the origin position coordinate is shifted within a second preset range and returned to the origin position.

In this embodiment, the second preset range may be understood as a preset offset range for the origin position coordinate, and may be, for example, a distance range within one quarter of the width (U/4) of the rectangular region.

Illustratively, the second preset range is (U/8~U/4). When at least one of the displacement of the origin position coordinate between the two adjacent periods and the displacement of the head position coordinate between the two adjacent periods does not meet the first preset range, that is, the displacement of the origin position coordinate and the displacement of the head position coordinate do not both meet the first preset range, in order to determine whether the to-be-monitored object rolled back to the origin after the body displaces, it is determined whether the origin position coordinate of the to-be-monitored object change, within a preset time (for example, one hour), from (X, Y)=(0, 0) to (U/8, 0)~(U/4, 0) or (−U/4, 0)~(−U/8, 0), and then back to (X, Y)=(0,0).

b2) The second result determining unit is specifically configured to determine the rollover detection result of the to-be-monitored object to be that a rollover event occurred if it is determined that the origin position coordinate is changed within the second preset range and returned to the origin position and the hand position coordinate is the same between the two adjacent periods.

Specifically, after it is determined that the origin position coordinate shifts within a preset time within a second preset range and then back to the origin position, it is determined whether the hand position coordinate is changed back to HN (x1, y1) or HN (x2, y2). If the hand position coordinate is changed back to the original coordinate, that is, the hand position coordinate is changed back to HN (x1, y1) or HN (x2, y2), it can be determined that the rollover detection result of the to-be-monitored object is that a rollover event occurred. If the hand position coordinate is not changed back to HN (x1, y1) or HN (x2, y2), it can be determined that a rollover event did not occur, and the rollover detection flow continues.

As a fourth alternative embodiment of the embodiment, on the basis of the above embodiments, as shown in FIG. 2, the alert module 14 is connected to the rollover detection subsystem 13, and includes a cloud information transceiving module 141, an emergency information call module 142 and a speaker 143.

The cloud information transceiving module 141 is configured to transceive cloud information, and the cloud information includes the rollover image and rollover alert information of the to-be-monitored object.

The emergency information call module 142 is configured to transmit the cloud information to an associated application.

The speaker 143 is configured to emit an alert sound.

In this embodiment, the cloud information transceiving module 141, the emergency information call module 142, and the speaker 143 are all directly connected to the rollover detection subsystem 13.

The cloud information transceiving module 141 is configured to transceive the rollover image and rollover alert information of the to-be-monitored object, and store the rollover image and the rollover alert information in a cloud. The rollover alert information is information that sends an alert prompt to a caregiver of the to-be-monitored object when the rollover detection result is that a rollover event occurred, and the rollover alert information may be alert prompt information such as text and/or sound.

The emergency information call module 142 is configured to transmit the cloud information to the associated application when the rollover detection result is that a rollover event occurred, so as to send a remote alert prompt to the caregiver of the to-be-monitored object.

The speaker 143 is configured to emit an alert sound when the rollover detection result is that a rollover event occurred, so as to give an alert prompt to the caregiver of the to-be-monitored object.

Figure 6:
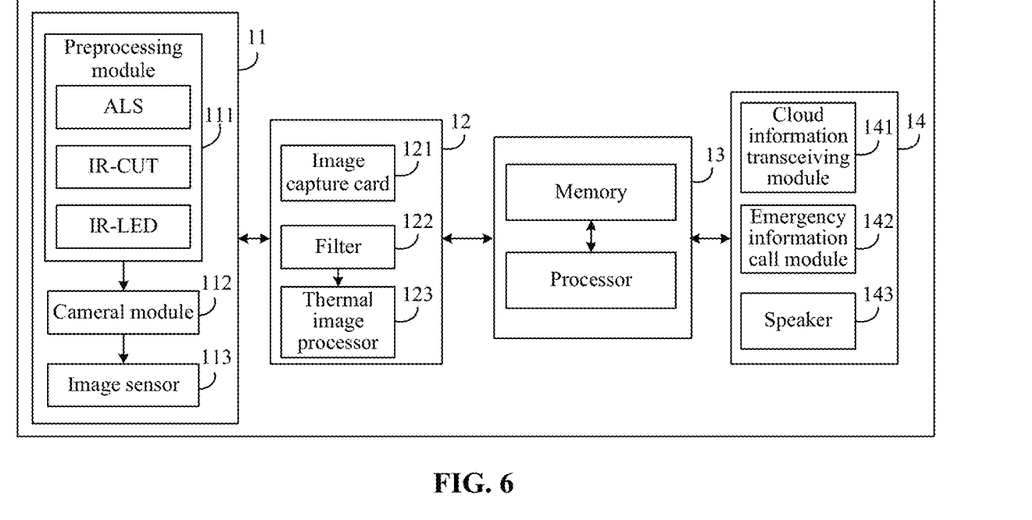
FIG. 6 is a block diagram showing illustratively the structure of a rollover detection system according to the first embodiment of the present invention.

Illustratively, for more clearly illustrating the rollover detection system, an illustrative block diagram of a structure of a rollover detection system as shown in FIG. 6 is set forth, the rollover detection subsystem 13 may include at least one processor and a memory in communication with the at least one processor. The body region segmentation module, the position information acquiring module and the detection result determining module may be understood as the processors, the image acquiring module may be understood as the memory, and a computer program executable by the at least one processor is stored in the memory to enable the at least one processor to perform the corresponding functions. In the rollover detection subsystem 13, there may be three processors in one-to-one correspondence to the body region segmentation module, the position information acquiring module, and the detection result determining module, respectively, to perform corresponding functions; there may be only one processor to perform all functions of the body region segmentation module, the position information acquiring module, and the detection result determining module, which is not limited in this embodiment.

Second Embodiment

Figure 7:
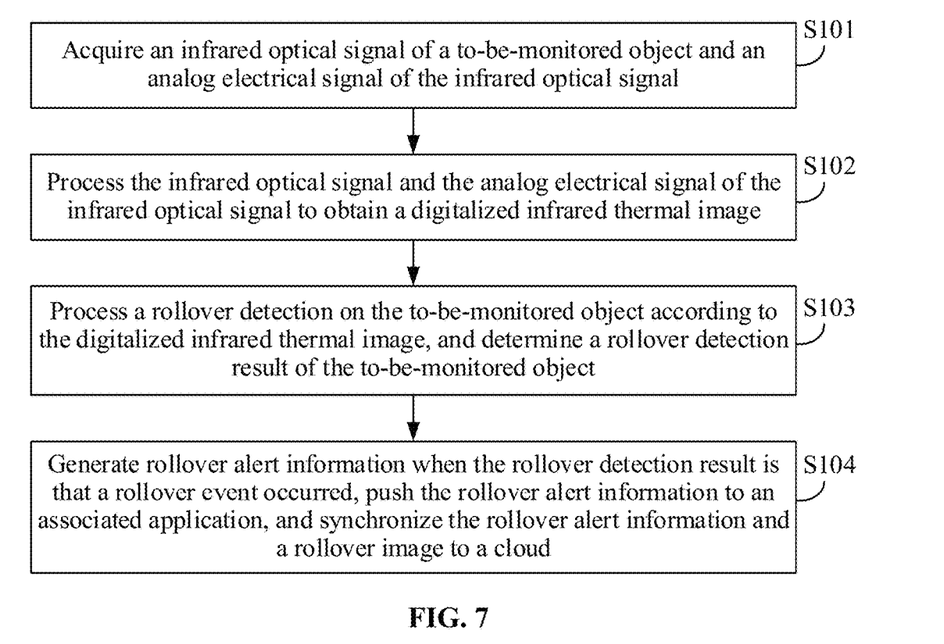
FIG. 7 is a flowchart of a rollover detection method according to a second embodiment of the present invention.

FIG. 7 is a flowchart of a rollover detection method according to a second embodiment of the present invention. The method is applicable to a case in which whether a to-be-monitored object rolled over is to be detected. The method may be performed by a rollover detection system, and the rollover detection system may be embodied in the form of a combination of hardware and software.

As shown in FIG. 7, the method includes as follows.

In S101, an infrared optical signal of a to-be-monitored object and an analog electrical signal of the infrared optical signal are acquired.

In this embodiment, when a rollover detection requirement for a to-be-monitored object is generated, an image acquiring module in the rollover detection system automatically acquires the infrared optical signal in a region where the to-be-monitored object is located, and converts the infrared optical signal into analog electrical signal, and transmits the converted analog electrical signal and the infrared optical signal to the image processing module for further image processing. The rollover detection requirement for the to-be-monitored object may be periodic cyclic acquisition requirements determined according to a preset period, or may be an acquisition requirement manually triggered by a related person through an associated application. A specific rollover detection requirement is determined according to practical conditions, which is not limited in this embodiment. It can be understood that the image acquiring module can always obtain clear infrared optical signal regardless of whether the ambient light is bright or dark.

In S102, the infrared optical signal and the analog electrical signal of the infrared optical signal are processed to obtain a digitalized infrared thermal image.

In this embodiment, the image processing module receives the infrared optical signal and the analog electrical signal of the infrared optical signal transmitted by the image acquiring module. After the infrared optical signal and the analog electrical signal are received, and in order to enable the rollover detection subsystem to more accurately implement the rollover detection on the to-be-monitored object, basic signal and image processing is performed on the analog electrical signal of the infrared optical signal in advance to obtain a digitalized infrared thermal image with clearer features. Specifically, the analog electrical signal is converted into a digital electrical signal, and corresponding basic image processing, such as filtering, denoising, enhancement or restoration, is performed on the received infrared thermal image. The processed digitalized infrared thermal image (digitalized information of the infrared thermal image) is transmitted to the rollover detection subsystem.

In S103, a rollover detection is performed on the to-be-monitored object according to the digitalized infrared thermal image, and a rollover detection result of the to-be-monitored object is determined.

In this embodiment, the rollover detection subsystem receives and stores the digitalized infrared thermal image transmitted by the image processing module and having subjected to the basic signal and image processing, and performs processing such as segmentation and feature extraction on the digitalized infrared thermal image to determine a body region of the to-be-monitored object and further determine a head region, a hand region, an origin position coordinate, a head position coordinate, and a hand position coordinate in the body region of the to-be-monitored object, and determines a rollover detection result of the to-be-monitored object according to the position changes of the head region and the hand region of the to-be-monitored object between two adjacent periods, and transmits the rollover detection result to the alert module after the rollover detection result of the to-be-monitored object is determined.

In S104, rollover alert information is generated when the rollover detection result is that a rollover event occurred, the rollover alert information is pushed to an associated application, and the rollover alert information and a rollover image are synchronized to a cloud.

In this embodiment, the alert module receives the rollover detection result transmitted by the rollover detection subsystem, and performs a corresponding execution operation according to the rollover detection result. When the rollover detection result is that a rollover event did not occur, the alert module does not operate; and when the rollover detection result is that a rollover event occurred, the alert module generates rollover alert information and synchronize the rollover alert information and the rollover image to a cloud so as to timely alert a caregiver and a related care mechanism of the to-be-monitored object, so that the caregiver and the related care mechanism can respond to the rollover event of the to-be-monitored object after receiving the rollover alert information, and take corresponding care of the to-be-monitored object in time.

In this embodiment, an infrared optical signal of a to-be-monitored object and an analog electrical signal of the infrared optical signal are acquired, by which an infrared thermal image of the to-be-monitored object and the analog electrical signal of the infrared thermal image are acquired; the infrared optical signal and the analog electrical signal of the infrared optical signal are processed to obtain a digitalized infrared thermal image, and a basic image process is performed on the infrared thermal image to obtain a processed infrared thermal image; a rollover detection is performed on the to-be-monitored object according to the digitalized infrared thermal image, and a rollover detection result of the to-be-monitored object is determined; rollover alert information is generated when the rollover detection result is that a rollover event occurred, the rollover alert information is pushed to an associated application, and the rollover alert information and the rollover image are synchronized to a cloud. According to the above technical solution, the infrared optical signal of the region where the to-be-monitored object is located can be acquired adaptively in various environments, corresponding image processing is performed in advance before the rollover detection is performed on the to-be-monitored object, to allow the digitalized infrared thermal image input to the rollover detection subsystem to be clearer in features; positions of the head region and the hand region of the to-be-monitored object are monitored, and the rollover detection result is determined according to the position offset of the head region and the hand region of the to-be-monitored object, thereby effectively enhancing the accuracy of the rollover detection, reducing the error of the rollover detection, and when the rollover detection result is that a rollover event occurred, alert information can be timely generated to notify the caregiver of the to-be-monitored object, thereby effectively improving the personal safety of the to-be-monitored object. With the above technical solution, a non-contact rollover detection on a to-be-monitored object is realized, the errors of the rollover detection are reduced, the accuracy of the rollover detection is improved, and the safety of the to-be-monitored object is guaranteed.

It should be appreciated that various forms of flows shown above may be used with the steps reordered, some added, or deleted. For example, the steps in the present invention may be performed in parallel, may be performed in sequence, or may be performed in different sequences, which is not limited herein as long as the expected result of the technical solutions of the present invention can be realized.

The above-mentioned embodiments do not constitute a limitation on the protection scope of the present invention. It is to be appreciated by the person skilled in the art that various modifications, combinations, sub-combinations, and substitutions may be made according to design requirements and other factors. Any modifications, equivalent substitutions, improvements and the like within the spirit and principle of the present invention shall fall within the protection scope of the present invention.

What is claimed is:

1. A rollover detection system, comprising an image acquiring module, an image processing module, a rollover detection subsystem, and an alert module; wherein
   the image acquiring module is configured to acquire an infrared optical signal of a to-be-monitored object and an analog electrical signal of the infrared optical signal and transmit the infrared optical signal and the analog electrical signal of the infrared optical signal to the image processing module;
   the image processing module is configured to process the infrared optical signal and the analog electrical signal of the infrared optical signal to obtain a digitalized infrared thermal image, and transmit the digitalized infrared thermal image to the rollover detection subsystem;
   the rollover detection subsystem is configured to perform a rollover detection on the to-be-monitored object according to the digitalized infrared thermal image, and determine a rollover detection result of the to-be-monitored object; and
   the alert module is configured to generate rollover alert information in response to determining that the rollover detection result is a rollover event, push the rollover alert information to an associated application, and synchronize the rollover alert information and a rollover image to a cloud.

2. The system according to claim 1, wherein the image acquiring module comprises a preprocessing module, a camera module, and an image sensor;
   the preprocessing module is configured to assist the camera module in acquiring an optical signal under a condition that illuminance is less than a preset value;
   the camera module is configured to acquire the optical signal; and
   the image sensor is configured to converge the optical signal and convert the optical signal into an analog electrical signal.

3. The system according to claim 1, wherein the image processing module comprises an image capture card, a filter, and a thermal image processor;
   the image capture card is configured to convert the analog electrical signal into digital electrical signal and perform image digitalization processing on the digital electrical signal to obtain a converted digital electrical signal, and transmit the converted digital electrical signal to the rollover detection subsystem to store the converted digital electrical signal;
   the filter is configured to perform filtering processing on the analog electrical signal to obtain a filtered analog electrical signal, and transmit the filtered analog electrical signal to the thermal image processor; and
   the thermal image processor is configured to convert the filtered analog electrical signal into a digital electrical signal and perform basic image processing on the digital electrical signal to generate the digitalized infrared thermal image, and transmit the digitalized infrared thermal image to the rollover detection subsystem.

4. The system according to claim 1, wherein the rollover detection subsystem comprises an image acquiring module, a body region segmentation module, a position information acquiring module, and a detection result determining module;
   the image acquiring module is configured to acquire the digitalized infrared thermal image of a to-be-monitored object according to a preset period;
   the body region segmentation module is configured to segment body regions of the to-be-monitored object in the digitalized infrared thermal image according to color temperatures of the digitalized infrared thermal image;
   the position information acquiring module is configured to determine a head region and a hand region of the to-be-monitored object from the body regions of the to-be-monitored object in the digitalized infrared thermal image, and relevant position information of the to-be-monitored object; and the relevant position information comprises an origin position coordinate, a head position coordinate, and a hand position coordinate; and the detection result determining module is configured to determine the rollover detection result of the to-be-monitored object according to a change of the related position information between two adjacent periods.

5. The system according to claim 4, wherein the position information acquiring module is configured to:
  determine, according to the body region of the to-be-monitored object, a rectangular region corresponding to the body region;
  determine a center point position of the to-be-monitored object according to a side length of the rectangular region, determine the center point position as an origin position, and obtain the origin position coordinate of the origin position;
  determine the head region and the hand region of the to-be-monitored object according to color temperatures in the rectangular region; and
  determine the head position coordinate and the hand position coordinate according to the origin position coordinate.

6. The system according to claim 4, wherein the detection result determining module comprises a displacement determining unit, a first result determining unit, and a second result determining unit;
  the displacement determining unit is configured to determine whether a displacement of the origin position coordinate between the two adjacent periods and a displacement of the head position coordinate between the two adjacent periods are within a first preset range;
  the first result determining unit is configured to determine that the rollover detection result of the to-be-monitored object is a rollover event, in response to determining that the displacement of the origin position coordinate between the two adjacent periods and the displacement of the head position coordinate between the two adjacent periods are within a first preset range and the hand position coordinate in the two adjacent periods are symmetric with respect to the center point position; and
  the second result determining unit is configured to determine the rollover detection result of the to-be-monitored object in response to determining that at least one of the displacement of the origin position coordinate between two adjacent periods and the displacement of the head position coordinate between two adjacent periods does not meet the first preset range.

7. The system according to claim 6, wherein the second result determining unit is configured to:
  determine, in response to determining that at least one of the displacement of the origin position coordinate between two adjacent periods and the displacement of the head position coordinate between two adjacent periods does not meet the first preset range, whether the origin position coordinate is shifted within a second preset range and returned to the origin position; and
  determine that the rollover detection result of the to-be-monitored object is the rollover event, in response to determining that the origin position coordinate is shifted within the second preset range and returned to the origin position and the hand position coordinates in two adjacent periods are same.

8. The system according to claim 1, wherein the alert module is connected to the rollover detection subsystem and the alert module comprises a cloud information transceiving module, an emergency information call module and a speaker;
  the cloud information transceiving module is configured to transceive cloud information, and the cloud information comprises the rollover image and rollover alert information of the to-be-monitored object;
  the emergency information call module is configured to transmit the cloud information to the associated application; and
  the speaker is configured to emit an alert sound.

9. A rollover detection method, comprising:
  acquiring an infrared optical signal of a to-be-monitored object and an analog electrical signal of the infrared optical signal;
  processing the infrared optical signal and the analog electrical signal of the infrared optical signal to obtain a digitalized infrared thermal image;
  performing a rollover detection on the to-be-monitored object according to the digitalized infrared thermal image, and determining a rollover detection result of the to-be-monitored object; and
  generating rollover alert information in response to determining that the rollover detection result is a rollover event, pushing the rollover alert information to an associated application, and synchronizing the rollover alert information and a rollover image to a cloud.

10. A non-transitory computer-readable storage medium, storing a computer instruction, wherein the computer instruction is used to cause a rollover detection system to implement the rollover detection method according to claim 9 when the rollover detection system performs the computer instruction.

* * * * *